US011369568B2

(12) United States Patent
O'Neil

(10) Patent No.: US 11,369,568 B2
(45) Date of Patent: *Jun. 28, 2022

(54) MICROPARTICLES COMPRISING A SULPHUR-CONTAINING COMPOUND

(71) Applicant: NOVABIOTICS LIMITED, Aberdeenshire (GB)

(72) Inventor: Deborah O'Neil, Aberdeenshire (GB)

(73) Assignee: NOVABIOTICS LIMITED, Aberdeenshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/307,990

(22) PCT Filed: Jun. 6, 2017

(86) PCT No.: PCT/GB2017/051637
§ 371 (c)(1),
(2) Date: Dec. 7, 2018

(87) PCT Pub. No.: WO2017/212249
PCT Pub. Date: Dec. 14, 2017

(65) Prior Publication Data
US 2019/0175501 A1  Jun. 13, 2019

Related U.S. Application Data

(60) Provisional application No. 62/346,969, filed on Jun. 7, 2016.

(30) Foreign Application Priority Data

Jun. 7, 2016 (GB) ..................................... 1609940

(51) Int. Cl.
| A61K 9/00 | (2006.01) |
| A61K 9/16 | (2006.01) |
| A61K 31/145 | (2006.01) |
| A61K 31/198 | (2006.01) |
| A61K 45/06 | (2006.01) |
| A61P 31/04 | (2006.01) |
| A61P 11/00 | (2006.01) |

(52) U.S. Cl.
CPC .......... *A61K 9/0075* (2013.01); *A61K 9/0073* (2013.01); *A61K 9/16* (2013.01); *A61K 9/1617* (2013.01); *A61K 9/1623* (2013.01); *A61K 31/145* (2013.01); *A61K 31/198* (2013.01); *A61K 45/06* (2013.01); *A61P 31/04* (2018.01)

(58) Field of Classification Search
None
See application file for complete search history.

(56) References Cited

U.S. PATENT DOCUMENTS

| 8,389,014 B2 | 3/2013 | Longo et al. |
| 8,415,398 B2 | 4/2013 | Liang et al. |
| 10,905,660 B2 * | 2/2021 | O'Neil ................. A61K 31/145 |
| 2012/0129946 A1 | 5/2012 | Thoene |
| 2012/0135969 A1 | 5/2012 | Weiler et al. |
| 2014/0275279 A1 * | 9/2014 | Eddy ....................... A61K 45/06 514/665 |
| 2019/0076368 A1 * | 3/2019 | Gazzaniga .............. A61P 39/02 |

FOREIGN PATENT DOCUMENTS

| CN | 105101955 A | 11/2015 |
| JP | 2014515356 A | 6/2014 |
| KR | 10-2014-0029372 A | 3/2014 |
| RU | 2013131391 A | 1/2015 |
| WO | 9013538 A1 | 11/1990 |
| WO | 2010091124 A2 | 8/2010 |
| WO | 2012-159103 A1 | 11/2012 |
| WO | 2013120086 A1 | 8/2013 |
| WO | 2016046523 A1 | 3/2016 |

OTHER PUBLICATIONS

Merck Manual, obtained online at: https://www.merckmanuals.com/professional, Lung Carcinoma, Asthma, COPD, 41 pages (2019).
Lechuga-Ballesteros et al., "Trileucine Improves Aerosol Performance and Stability of Spray-Dried Powders for Inhalation", Journal of Pharmaceutical Sciences, 97(1), pp. 287-302 (Jan. 2008).
Cai et al., "Preparation, characterization and pulmonary pharmacokinetics of a new inhalable zanamivir dry powder", Drug Delivery, 23(6), pp. 1962-1971 (Jun. 11, 2015).
Li et al., Journal of Aerosol Medicine and Pulmonary Drug Delivery, 27(2), pp. 81-93 (2014).
Charrier et al., Orphanet Journal of Rare Diseases, 9(189), pp. 1-11 (2014).
Flume et al., Am J Respir Crit Care Med, 176, pp. 957-969 (2007).
Buchan, B.E., "Formulation Studies on Cysteamine For The Treatment of Nephropathic Cystinosis", Aug. 1, 2011, pp. 1-223, XP55404192, Retrieved from the Internet: URL:https://core.ac.uk.download/pdf/1576960.pdf [retrieved on Sep. 6, 2017].
Buchan, B.E., "The formulation and evaluation of a dry powder for pulmonary delivery in cystinosis", Jan. 1, 2010, XP55403968, Retrieved from Internet: URL:https://www.cystinosis.org.uk/wp-content/uploads/2010/09/2010_RGU_Research Poster.pdf [retrieved on Sep. 5, 2017].
Lockhart, S.P., Inhaled thiol and phosphorothiol radioprotectors fail to protect the mouse lung:, Radiotherapy and Oncology, vol. 19, No. 2, Oct. 1, 1990, pp. 187-191, XP55404166, Ireland, ISSN: 0167-8140, DOI: 10:1016/0167-8140(90)90132-G.
Charrier, Cedric et al., "Cysteamine (Lynovex?), a novel mucoactive antimicrobial & antibiofilm agent for the treatment of cystic fibrosis", Orphanet Journal of Rare Diseases, Biomed Central Ltd., LO, vol. 9, No. 1, Nov. 30, 2014, p. 189, XP021206325, ISSN: 1750-1172, DOI: 10.1186/S13023-014-0189-2.

(Continued)

*Primary Examiner* — Sin J Lee
(74) *Attorney, Agent, or Firm* — DLA Piper LLP (US)

(57) ABSTRACT

The present invention provides microparticles comprising a sulphur-containing compound, such as cysteamine, or a pharmaceutically acceptable salt, hydrate or ester thereof. Also provided is a composition comprising the microparticles and a stabilizing agent.

16 Claims, 6 Drawing Sheets

(56) References Cited

OTHER PUBLICATIONS

International Search Report and Written Opinion for PCT/GB2017/051637 dated Sep. 15, 2017.
Examination Report dated Dec. 16, 2020 for corresponding European Patent Application No. 17735616.9.
Examination Report dated Nov. 24, 2020 for corresponding Indian Patent Application No. 201817044232.
Office Action from the Russian Patent Office for Application No. 2018142841 dated Sep. 30, 2020 with English Translation.
English Translation of Examination report dated Feb. 20, 2021 on corresponding Russian application 2018142841.
English Translation of Examination report dated Feb. 18, 2021 on corresponding Mexican application MX/A/2018/014278.
Chinese Patent Application No. 2017800353607 Office Action (and English translation) dated Aug. 25, 2021.
Korean Patent Application No. 10-2018-7035476 Office Action (and English translation) dated Sep. 24, 2021.
Third Chinese Office Action and English Translation for corresponding Chinese Patent Application No. 201780035360.7 dated Jan. 30, 2022.
Japanese Office Action and English translation for corresponding Japanese Patent Application No. JP 2018-563831 dated Apr. 19, 2022.

* cited by examiner

MICROPARTICLES COMPRISING A SULPHUR-CONTAINING COMPOUND

CROSS-REFERENCE TO RELATED APPLICATIONS

This application is a U.S. national stage filing under 35 U.S.C. § 371 of International Application No. PCT/GB2017/051637 filed Jun. 6, 2017 entitled "MICROPARTICLES COMPRISING A SULPHUR-CONTAINING COMPOUND," which claims priority of U.S. Provisional Application No. 62/346,969 filed Jun. 7, 2016 and G.B. Application No. 1609940.0 filed Jun. 7, 2016, the disclosures of which are incorporated herein by reference in their entirety.

FIELD OF THE INVENTION

The present invention relates to microparticles comprising a sulphur-containing compound, such as cysteamine or cystamine, or a pharmaceutically acceptable salt, hydrate or ester thereof.

BACKGROUND TO THE INVENTION

Cystic fibrosis (CF) is a multisystem disorder caused by mutations in the cystic fibrosis transmembrane conductance regulator (CFTR) gene, located on chromosome.

Lung disease remains the leading cause of morbidity and mortality in patients with CF [Davis P B, Drumm M, Konstan M W. Cystic fibrosis. Am J Respir Crit Care Med 1996; 154:1229; Goss C H, Rosenfeld M. Update on cystic fibrosis epidemiology; Curr Opin Pulm Med 2004; 10:510; Brennan A L, Geddes D M. Cystic fibrosis. Curr Opin Infect Dis 2002; 15:175; Gibson R L, Burns J L, Ramsey B W. Pathophysiology and management of pulmonary infections in cystic fibrosis. Am J Respir Crit Care Med 2003; 168:918.

One of the major drivers of CF lung disease is infection (Sagel S D, Gibson R L, Emerson J, et al. Impact of *Pseudomonas* and *Staphylococcus* infection on inflammation and clinical status in young children with cystic fibrosis. J Pediatr 2009; 154:183; Cystic Fibrosis Foundation Annual Patient Registry 2013. Available at: http://www.cff.org/research/ClinicalResearch/PatientRegistryReport/(Accessed on Aug. 7, 2015).

The approach to treating infection in CF is multifaceted, involving antibiotics, chest physiotherapy, inhaled medications to promote secretion clearance, and anti-inflammatory agents. Undoubtedly, improved use of antibiotics is responsible for a substantial portion of the increased survival that has occurred in patients with CF (Brennan A L, Geddes D M. Cystic fibrosis. Curr Opin Infect Dis 2002; 15:175; Sagel S D, Gibson R L, Emerson J, et al. Impact of *Pseudomonas* and *Staphylococcus* infection on inflammation and clinical status in young children with cystic fibrosis. J Pediatr 2009; 154:183).

There remains a need for better therapies for treating and preventing lung diseases/conditions in particular those associated with mucous-rich environments such as the CF lung. In addition there remains a need to limit the amount or doses of antibiotics used with the introduction of novel, replacement therapies or adjunct treatments that can improve the effectiveness of currently available treatments in the treatment or prevention of bacterial infections, in particular in the CF lung.

Surprisingly, we have shown that microparticles provide a useful mode of delivery for cysteamine to patients with lung disease.

STATEMENTS OF THE INVENTION

According to a first aspect of the present invention there is provided a microparticle or microparticles comprising a sulphur-containing compound, or a pharmaceutically acceptable salt, hydrate or ester thereof.

As used herein "sulphur-containing compound" is intended to cover cysteamine, cystamine or a derivative thereof. The sulphur-containing compound may be an aminothiol. Examples of aminothiols include cysteamine and derivatives thereof. The term "derivative thereof" may encompass 2-methylthio ethylamine (cinnamate), 2-methyl thio ethylurea, N-(2-methylthio ethyl) p-acetamido benzamide, 2-aminoethanethiol, N-(2-methylthio ethyl)p-acetamido benzenesulfonamide, N-(2-propylthioethyl)-p-methoxy benzamide, N-(butylthio ethyl) nicotinamide, N-(2-dodecylthio ethyl) p-butoxybenzamide, N-(2-methylthio ethyl) p-toluenesulfonamide, N-(2-isopropylthio ethyl) propionamide. N-(2-octylthio ethyl) acetamide, N-(2-butylthio ethyl) methanesulfonamide, N-(2-isopentylthioethyl) butane, bis 1,4-(2-acetamido ethylthio), 2,3-butanediol, 2-hexadecylthio ethylamine hydrochloride, 2-allylthio ethylamine malate, 9-octadecene 2-ylthio ethylamine hydrochloride, 2-dodecylthio ethylamine hydrochloride, 2-isopentylthio ethylamine mandelate, 2-octadecylthio ethylamine salicylate, 2-.beta.-hydroxyethyl thio ethylurea, 2-.beta.-hydroxyethylthio ethylamine hydrochloride, 2-(2,3-dihydroxy propylthio)ethylamine p-toluenesulfonate, 2-(2-hydroxypropylthio)elhylamineoxalate, N-(2-methylthio ethyl (phenylacetamide, 2-(2,2-dimethoxy ethylthio) ethylamine hydrochloride, 2-(2,2-dimethoxy ethylthio) ethylamineundecylenate, 2-(2,2-diethoxy ethylthio) ethylamine undecylenate, 2-(2,2-diethoxy ethylthio)ethylamine acetate, 2-undecenylthio ethylamine, 2-.beta.-ureidoethylthio ethylamine hydrochloride, 2-.beta.-acetamidoethylthio ethylamine tropate, 2,2'-thio diethylamine fumarate, 2,2'-thio diethylurea, 3-.beta.-aminoethylthio propylamine hydrochloride, S-.beta.-ureidoethyl thiocarbamate, 2-ethoxycarbonylthio ethylamine hydrochloride, 2-dimethylamino carbonylthio ethylamine sulfate, 2-butoxycarbonyl methylthio ethylurea, 2-ethyloxycarbonylmethylthio ethylamine hydrochloride, 6-.beta.-aminoethylthio hexanoate of methyl hydrochloride, 5-.beta.-aminoethylthio pentanoic acid, 2-phenylthio ethylamine dihydrogen phosphate, 2-p-t-butylphenylthio ethylamine trichloracetate, 2-p-methoxyphenylthio ethylamine ditartrate, 2-tolylthio ethylamine hydrobromide, 2-(1-biphenyl thio) ethylamine hydrochloride, 2-N-pentachlorophenylthio ethyl acetamide, 2-benzylthio ethylamine malate, 2-benzylthio ethylamine nicotinate, 2-benzylthio 2-methyl propylamine hydrochloride, 2-benzylthio propylamine lactate, N-(2-benzylthio ethyl)nicotinamide hydrochloride, N-(2-benzylthio ethyl) 10-undecene amide, N-(2-benzylthio ethyl) hexadecanamide, S-.beta.-aminoethyl mercaptobutyric acid, N-(2-benzylthio ethyl)formamide, N-(2-benzylthio ethyl)phenyl acetamide, N-[2-(2,6-dimethyl phenyl) ethyl] hexanamide, 2-o-aminophenylthio ethylamine succinate, N-(2-benzylthio ethyl) glutamine, S-.beta.-aminoethyl mercapto acetic acid (3-S-.beta.-aminoethyl) mercapto propionic acid, (3-S-.gamma.-amino propyl) mercapto acetic acid, S(2-p-methoxybenzamido ethyl) mercapto 2-(2-naphtyl methylthio) ethylamine hydrochloride, 2-(2-naphtyl methylthio) ethylamine disuccinate, (2-thenyl) 2-thio ethylamine hydrobromide, 2-N-acetyl (2-thenylthio-ethylamine, 2-o-chlorobenzylthio ethylamine hydrochloride, 2-p-chlorobenzylthio ethylamine glycolate, 2-o-fluorobenzylthio ethylamine hydrochloride, 2-furfurylthio ethylamine hydrochloride, 2-tetrahydrofurfurylthio ethylamine p-amino-benzoate, 2-.beta.-phenyl ethylthio ethylamine glutamate, 2-diphenyl methylthio ethylamine hydrochloride, 2-triphenyl methylthio ethylamine hydrochloride hemihydrate, 2-(2-pyridylethylthio)ethylamine hydrochloride, 2-(2-p-toluene sulfonamido ethylthio) pyridine N-oxide, 2-.beta.-aminoethylthiomethyl pyridine N-oxide dihydrochloride, 2-.beta.-aminoethylthio pyridine N-oxide hydrochloride, 2,4-dichloro 2-benzylthio ethylamine aspartate, N-[2-(3,4-dichloro benzylthio)ethyl] butyramide, N-[2-(2,6-dichloro benzylthio)ethyl] dodecanamide, N-[2-(3,5-dichloro benzylthio)ethyl] trifluoroacetamide hydrochloride, 2-p-ethoxybenzylthio ethylamine hydrochloride, N-[2-m-fluorobenzylthio ethyl] chloroacetamide, 2-p-bromobenzylthio ethylamine succinate, 2-(3,4-dimethoxy benzylthio)ethylamine malate, 2-(3,4-methylenedioxy benzylthio)ethylamine hydrochloride, 2-(2,4-dichloro cetylthio)ethylamine, 2(3,4,5-trimethoxy benzylthio)ethylamine hydrocinnamate, 2-p-methoxy benzylthio ethylamine salicylate, 2-o-methylbenzylthio ethylamine phenyl-acetate, N-[2-p-dimethylaminobenzylthio ethyl] methane-sulfonamide, 2-p-phenoxybenzylthio ethyl amine hydrochloride, 2-.beta.-aminoethylthio pyridine hydrochloride, 2-benzylthio ethylamine citrate, N-[2-benzylthio ethyl] 2,4-dihydroxy 3,3-dimethyl butyramide, N-(2-benzylthio ethyl) 6,8-dihydroxy 7,7-dimethyl 5-oxo 4-aza octanamide, N-[2-(2-pyridyl thio)ethyl] propionamide, 2-(2-pyridyl methylthio)ethylamine dihydrochloride, 2-benzylthio ethylamine pantothenate, S-(.beta.-acetamidoethyl)mercapto acetate of beta.-morpholinoethyl, S-(.beta.-phenyl acetamidoethyl)mercapto acetate N'-methyl 2-piperazino ethyl, S-(.beta.-ureidoethyl)mercaptoacetate of beta.-pyrrolidino-ethy, S-(.beta.-trifluoroacetamidoethyl)-.beta.mercapto-propionate of .beta.-dimethyl aminoethyl, 2-p-nitrobenzylthio ethylamine crotonate, 2-.beta.-morpholinocarbonyl ethylthio ethylamine hydrochloride, N,N-di (hydroxyethyl) S-(.beta.-benzamido-ethyl) mercapto-acetamido, N [2-N'-methyl piperazino carbonylthio ethyl] acetamide, 2-(1-naphthyl thio)ethylamine hydrochloride, N-(3-.beta.-ureidoethylthio propyl) succinamic acid, 3-allylthio propylamine, 3-(2,2'-dimethoxy ethylthio)propylamine, 3-(2,2'-dimethoxy ethylthio)propyl amine sulfate, S-.beta.-aminoethyl mercapto acetic acid, the hydrochloride of S-.beta.-aminoethyl mercapto acetic acid, N-(2-benzylthioethyl)acetamide, N-(2-benzylthioethyl)propionamide, N-(2-benzylthioethyl)butyramide, N-(2-benzylthioethyl) methane sulfonamide, N-(2-benzylthioethyl)ethanesulfonamide, N-(2-benzylthioethyl-propane sulfonamide, N-(2-benzylthioethyl)butanesulfonamide, S-(2-p-acetamidobenzenesulfonamido ethyl) mercapto acetic acid, S-(2-p-acetamidobenzamido ethyl) mercapto acetic acid, N-(2-thenylthioethyl)acetamide, 2-b enzylthio propylamine, 2-benzylthio 2-methyl propyl amine, 2-(2-p-toluenesulfonamido ethylthio) pyridine N-oxide, S-(2-p-butoxybenzamidoethyl)mercapto acetic acid, 2-t-butylthio ethylamine hydrochloride, 2-methoxycarbonylmethylthio ethylamine hydrochloride, 2-ethoxycarbonylmethylthio ethylamine hydrochloride, 2-propoxycarbonylmethyl thio ethylamine hydrochloride, 2-butoxycarbonylmethylthio ethyl amine hydrochloride, 2,2'-thio diethylamine dihydrochloride, 3-(2-aminoethylthio)alanine hydrochloride, 2-benzylthio ethyl ammonium diacid phosphate, 2-methylthio ethylamine, N-(methylthio ethyl) p-acetamidobenzamide, N-(2-methylthioethyl)nicotinamide, N-(2-methylthioethyl)benzamide, N-(2-methylthioethyl) p-butoxybenzamide, N-(2-methylthioethyl) butyramide, N-(2-methylthioethyl) propionamide, N-(2-methylthioethyl) acetamide, N-(2-methylthioethyl) butane sulfonamide, N-(2-octylthioethyl) methane sulfonamide, 2-cetylthio ethylamine hydrochloride, 2-(2-hydroxyethylthio) ethylamine hydrochloride, 2-methylthio ethyl amine phenyl acetate and 2-methylthio ethylamine undecylenate.

Alternatively, the sulphur-containing compound may be an organic disulphide, such as cystamine.

The sulphur-containing compound of the invention may be administered in the form of pharmaceutically acceptable salts. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., US, 1985, p. 1418, the disclosure of which is hereby incorporated by reference; see also Stahl et al, Eds, "*Handbook of Pharmaceutical Salts Properties Selection and Use*", Verlag Helvetica Chimica Acta and Wiley-VCH, 2002. The phrase "pharmaceutically acceptable" is employed herein to refer to those compounds, materials, compositions, and/or dosage forms which are, within the scope of sound medical judgment, suitable for use in contact with the tissues of human beings or, as the case may be, an animal without excessive toxicity, irritation, allergic response, or other problem or complication, commensurate with a reasonable benefit/risk ratio.

The invention thus includes pharmaceutically-acceptable salts of the disclosed compounds wherein the parent compound is modified by making acid or base salts thereof for example the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

In a preferred aspect of the invention, the microparticles have particle size of about 0.5 to 15 microns, for example 1 to 13 microns, including 4 to 8 microns. Particle size may be defined as "volume mean diameter" and as such the microparticles may have a volume mean diameter of about 0.5 to 15 microns, for example 1 to 13 microns, including 4 to 8 microns. The microparticles may have a volume mean diameter of 2 to 4 microns/micrometers (2-4 μm).

Mean is a calculated value similar to the concept of average. The various mean calculations are defined in several standard documents (ISO 9276-2:2001: Representation of results of particle size analysis—Part 2: Calculation of average particle sizes/diameters and moments from particle size distributions; ASTM E 799-03 Standard Practice for Determining Data Criteria and Processing for Liquid Drop Size Analysis). There are multiple definitions for mean because the mean value is associated with the basis of the distribution calculation (number, surface, volume), see (TN154, Particle Size Result Interpretation: Number vs. Volume Distributions, available at www.horiba.com/us/particle) for an explanation of number, surface, and volume distributions. The equation for defining the volume mean is shown below. The best way to think about this calculation is to think of a histogram table showing the upper and lower limits of n size channels along with the percent within this channel. The $D_i$ value for each channel is the geometric mean, the square root of upper×lower diameters. For the numerator take the geometric $D_i$ to the fourth power multiplied by the percent in that channel, summed over all channels. For the denominator take the geometric $D_i$ to the third power multiplied by the percent in that channel, summed over all channels.

$$D[4,3] = \frac{\sum_{1}^{n} D_i^4 v_i}{\sum_{1}^{n} D_i^3 v_i}$$

The volume mean diameter has several names including D4,3 or D50/D90.

As used herein, the terms "diameter" or "d" in reference to particles refers to the number average particle size, unless otherwise specified. An example of an equation that can be used to describe the number average particle size is shown below:

$$d = \frac{\sum_{i=1}^{p} n_i d_i}{\sum_{i=1}^{p} n_i}$$

where n=number of particles of a given diameter (d).

As used herein, the terms "geometric size", "geometric diameter, "volume average size", "volume average diameter" or "dg" refers to the volume weighted diameter average. An example of equations that can be used to describe the volume average diameter is shown below:

$$d_g = \left[ \frac{\sum_{i=1}^{p} n_i d_i^3}{\sum_{i=1}^{p} n_i} \right]^{1/3}$$

where n=number of particles of a given diameter (d).

As used herein, the term "volume median" refers to the median diameter value of the "volume-weighted" distribution. The median is the diameter for which 505 of the total are smaller and 50% are larger and corresponds to a cumulative fraction of 50%.

Geometric particle size analysis can be performed on a Coulter counter, by light scattering, by light microscopy, scanning electron microscopy, or transmittance electron microscopy, as known in the art. It is a generally held belief that the ideal scenario for delivery to the lung is to have an aerodynamic diameter <5 micrometers. See, e.g., Edwards et al., J Appl. Physiol. 85(2):379-85 (1998); Suarez & Hickey, Respir. Care. 45(6):652-66 (2000).

As used herein, the term "aerodynamic diameter" refers to the equivalent diameter of a sphere with density of 1 g/mL were it to fall under gravity with the same velocity as the particle analysed. The aerodynamic diameter ($d_a$) of a microparticle is related to the geometric diameter (dg) and the envelope density ($p_e$) by the following:

$$da = dg\sqrt{\rho e}$$

Porosity affects envelope density which in turn affects aerodynamic diameter. Thus porosity can be used to affect both where the microparticles go in the lung and the rate at which the microparticles release the pharmaceutical agent in the lung. Gravitational settling (sedimentation), inertial impaction, Brownian diffusion, interception and electrostatic affect particle deposition in the lungs.

The microparticles may have an aerodynamic diameter of about 0.5 to 15 microns, for example 1 to 13 microns, including 4 to 8 microns. The microparticles may have an aerodynamic diameter of 2 to 4 microns/micrometers (2-4 µm).

In a further aspect, the invention provides a composition comprising microparticles according to the first aspect of the invention and a stabilizing agent. In some instances the stabilizing agent is selected from the group consisting of monosaccharides, disaccharides, trisaccharides, oligosaccharides and their corresponding sugar alcohols, polysaccharides and chemically modified carbohydrates.

In a yet further aspect, the invention provides a composition comprising a sulphur-containing compound, or a pharmaceutically acceptable salt, hydrate or ester thereof, and a stabilizing agent as defined herein.

The stabilizing agent may be a sugar such as trehalose.

The stabilising agent may be a sugar alcohol selected from the group consisting of lactose, erythritol, ribitol, xylitol, galactitol, glucitol and mannitol. Preferably the stabilising agent is mannitol.

In a preferred composition of the invention, the composition comprises up to 20%w/w sulphur-containing compound, for example between 1 and 15% such as between about 5 and 10% w/w Sulphur-containing compound. Typically, the composition comprises about 5 or 10% Sulphur-containing compound.

As used herein, the term "about" is intended to vary the specified amount to allow for minor fluctuations of between + or 10% of the specified amount.

In a preferred composition of the invention, the composition comprises up to 85% stabilising agent. The composition may comprise between 80 and 95% w/w stabilizing agent, for example between 85 and 90% w/w stabilizing agent. Typically, the composition comprises about 90% stabilizing agent.

It has been shown that in compositions according to the invention which comprise trehalose or mannitol, cysteamine has increased formulation stability.

In a preferred embodiment of the invention the sulphur-containing compound is cysteamine or cystamine, preferably cysteamine. In a further embodiment of the invention, the sulphur-containing compound is cysteamine bitartrate.

In a preferred embodiment the composition is provided as an aqueous composition.

The composition of the invention may further comprise leucine. Leucine has surprisingly been shown to improve the stability of the formulation. In one embodiment of the invention, the composition comprises between 1 and 10% leucine, preferably about 5% leucine.

The composition may be in a solid dose form selected from the group consisting of microparticles, microspheres, and powders. Preferably the composition is provided as a dry powder. The powder may contain particles having a geometric diameter of about 3 to 8 microns, including 4 to 8 microns, such as 3 to 7 microns. In one embodiment, the powder contains particles having a geometric diameter of up to about 5 microns, for example 2 to 4 microns.

A further aspect of the invention provides microparticles according to the first aspect of the invention, or a composition according to the invention, for use in the treatment or prevention of lung disease.

A yet further aspect of the present invention relates to a method of treating or preventing lung disease comprising administering microparticles according to the first aspect of the invention, or a composition according to the invention, to a subject suffering, or having previously suffered from, from lung disease.

As used herein the term "lung disease" includes any disease or condition of the lung including cystic fibrosis, specifically lung infections associated with cystic fibrosis, and chronic obstructive pulmonary disease (COPD). COPD is the name for a collection of lung diseases including chronic bronchitis, bronchiectasis, emphysema and chronic obstructive airways disease. The term lung disease is also intended to include any respiratory disease which has a mucous or infectious element, for example a chronic cough, common cold, influenza, hantavirus, pneumonia and pleurisy.

A further aspect of the invention provides a therapeutic composition (or combination) which may be useful in the treatment or prevention of lung disease, which comprises microparticles according to the first aspect of the invention, or a composition according to the invention, and at least one additional pharmaceutical agent. The additional pharmaceutical agent may be selected from the group consisting of antimicrobial agents such as antiviral, antifungal or antibacterial agents e.g. antibiotics, mucolytic agents, vasodilators such as bronchidilators, antihypertensive agents, cardiovascular drugs and calcium channel blockers. Preferably the additional pharmaceutical agent is an antibiotic.

The term "antibiotic" is used to refer to antibacterial agents that may be derived from bacterial sources. Antibiotic agents may be bactericidal and/or bacteriostatic.

The antibiotic agent may contain a β-lactam ring. The β-lactam ring is part of the core structure of several antibiotic families, the principal ones being the penicillins, cephalosporins, carbapenems, and monobactams. These antibiotic agent are called β-lactam antibiotics.

Generally the antibiotic agent is of the group consisting of aminoglycosides, ansamycins, carbacephem, β-lactams carbapenems, cephalosporins, (including first, second, third, fourth and fifth generation cephalosporins), penicillin, monobactams), glycylcyclines, lincosamides, lipopeptides, macrolides, nitrofurans, oxazolidinones, quinolones, sulfonamides, polypeptides and tetracyclins.

The antibiotic agent may be of the group consisting of aminoglycosides, ansamycins, carbacephem, carbapenems, cephalosporins (including first, second, third, fourth and fifth generation cephalosporins), lincosamides, macrolides, monobactams, nitrofurans, quinolones, penicillin, sulfonamides, polypeptides and tetraclyins. Alternatively or additionally the antibiotic agent may be effective against mycobacteria.

The antibiotic agent may be an aminoglycoside such as Amikacin, Gentamicin, Kanamycin, Neomycin, Netilmicin, Tobramycin or Paromomycin.

The antibiotic agent may be an http://en.wikipedia.org/wiki/Ansamycin such as Geldanamycin and Herbimycin Alternatively the antibiotic agent may be a carbacephem such as Loracarbef.

The antibiotic agent is a carbapenem such as Ertapenem, Doripenem, Imipenem/Cilastatin or Meropenem.

Alternatively the antibiotic agent may be a cephalosporins (first generation) such as Cefadroxil, Cefazolin, Cefalexin, Cefalotin or Cefalothin, or alternatively a Cephalosporins (second generation) such as Cefaclor, Cefamandole, Cefoxitin, Cefprozil or Cefuroxime. Alternatively the antibiotic agent may be a Cephalosporins (third generation) such as Cefixime, Cefdinir, Cefditoren, Cefoperazone, Cefotaxime, Cefpodoxime, Ceftibuten, Ceftizoxime and Ceftriaxone or a Cephalosporins (fourth generation) such as Cefepime and Ceftobiprole.

The antibiotic agent may be a lincosamides such as Clindamycin and Azithromycin, or a macrolide such as Azithromycin, Clarithromycin, Dirithromycin, Erythromycin, Roxithromycin, Troleandomycin, Telithromycin and Spectinomycin.

Alternatively the antibiotic agent may be a monobactams such as Aztreonam, or a nitrofuran such as Furazolidone or Nitrofurantoin.

The antibiotic agent may be a penicillin such as Amoxicillin, Ampicillin, Azlocillin, Carbenicillin, Cloxacillin, Dicloxacillin, Flucloxacillin, Mezlocillin, Nafcillin, Oxacillin, Penicillin G or V, Piperacillin, Temocillin and Ticarcillin.

The antibiotic agent may be an oxazolidinone such as linezolid or tedizolid.

The antibiotic agent may be a sulfonamide such as Mafenide, Sulfonamidochrysoidine, Sulfacetamide, Sulfadiazine, Silver sulfadiazine, Sulfamethizole, Sulfamethoxazole, Sulfanilimide, Sulfasalazine, Sulfisoxazole, Trimethoprim, and Trimethoprim-Sulfamethoxazole (Co-trimoxazole) (TMP-SMX).

The antibiotic agent may be a quinolone such as Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin and Temafloxacin.

The antibiotic agent may be a polypeptide. Examples of such polypeptides include Bacitracin, Colistin and Polymyxin B. In one embodiment, the antibiotic agent is not a polypeptide.

The antibiotic agent may be a lipopeptide. Examples of such lipopeptides include Daptomycin and Surfactin.

Alternatively, the antibiotic agent may be a tetracycline such as Demeclocycline, Doxycycline, Minocycline and Oxytetracycline Alternatively the antibiotic agent may be a glycylcycline. Examples of such glycylcyclines include tigecycline.

Alternatively or additionally the antibiotic agent may be effective against mycobacteria. In particular the antibiotic agent may be Clofazimine, Lamprene, Dapsone, Capreomycin, Cycloserine, Ethambutol, Ethionamide, Isoniazid, Pyrazinamide, Rifampicin, Rifabutin, Rifapentine or Streptomycin.

In one embodiment, the antibiotic agent is a macrolide and/or an aminoglycoside and/or sulphonamides.

In one embodiment, the antibiotic is selected from tobramycin, azithromycin, telithromycin, ciproflaxin, ceftazidime.

In one embodiment, the antibiotic agent is not ciproflaxin. In another embodiment the antibiotic is not tobramycin.

The antibiotic agent may be active in the treatment or prophylaxis of infections caused by Enterobacteriaceae (e.g. *E. coli* or *Klebsiella* spp., such as *K. pneumoniae*) or non-Enterobacteriaceae bacteria such as *Burkholderia* spp.

Generally the antibiotic agent is active in the treatment or prophylaxis of infections caused by gram-negative or gram-positive bacteria, such as *Pseudomonas* spp.

In one embodiment of the invention, the antibiotic is not a β-lactam antibiotic.

The active agents of the invention may be provided as pharmaceutical compositions additionally containing one or more pharmaceutically acceptable diluents, excipients and/or carriers. For example, the additional pharmaceutical agent may be provided as a composition comprising the agent and a carrier such as lactose or mannitol.

In a preferred aspect of the invention, the microparticles, or the composition, according to the invention, and the additional pharmaceutical agent may be administered simultaneously, sequentially or separately. The microparticles, or composition, and additional pharmaceutical agent may be provided as a combination package. The combination package may further comprise instructions for simultaneous, separate or sequential administration of each of the microparticles, or composition, and additional pharmaceutical agent. For sequential administration, the microparticles, or composition, and additional pharmaceutical agent can be administered in any order.

The at least one additional pharmaceutical agent may be provided in microparticles distinct from said microparticles of the first aspect of the invention. Alternatively, the at least one additional pharmaceutical agent may be provided in a form other than microparticles.

In one embodiment of the invention, the microparticles of the first aspect of the invention, or composition according to the invention, comprise the at least one additional pharmaceutical agent.

In a further embodiment of the invention, the at least one additional pharmaceutical agent is administered in microparticles distinct from the microparticles of the first aspect, or composition, of the invention.

In a yet further embodiment of the invention, the at least one additional pharmaceutical agent is administered in a form other than microparticles.

In one embodiment, the microparticles or composition of the invention comprising a sulphur-containing compound, such as cysteamine, and/or an additional pharmaceutical agent to be administered in addition to the sulphur-containing compound have a volume average diameter between 0.1 and 5 micrometers (e.g., between 1 and 5 micrometers, between 2 and 5 micrometers, etc.). In another embodiment, the microparticles or composition of the invention, and/or an additional pharmaceutical agent, have a volume average diameter of up to 10 micrometers, for targeting delivery to the large bronchi. Particle size (geometric diameter and aerodynamic diameter) is selected to provide an easily dispersed powder that upon aerosolization and inhalation readily deposits at a targeted site in the respiratory tract (e.g., upper airway, deep lung, etc.), preferably while avoiding or minimizing excessive deposition of the particles in the oropharyngel or nasal regions. In one preferred embodiment, the porous microparticles have a volume average diameter of between 2 and 5 micrometers, for example between 2 and 4 micrometers.

Considerable attention has been devoted to the design of therapeutic aerosol inhalers to improve the efficiency of inhalation therapies. Timsina et. al., Int. J Pharm., 101: 1-13 (1995); and Tansey, I. P., Spray Technol. Market, 4: 26-29 (1994). Attention has also been given to the design of dry powder aerosol surface texture, regarding particularly the need to avoid particle aggregation, a phenomenon which considerably diminishes the efficiency of inhalation therapies. French, D. L., Edwards, D. A. and Niven, R. W., J. Aerosol ScL, 27: 769-783 (1996). Dry powder formulations ("DPFs") with large particle size have improved flowability characteristics, such as less aggregation (Visser, J., Powder Technology 58: 1-10 (1989)), easier aerosolization, and potentially less phagocytosis. Rudt, S. and R. H. Muller, J. Controlled Release, 22: 263-272 (1992); Tabata, Y. and Y. Bcada, J. Biomed. Mater. Res., 22: 837-858 (1988). Dry powder aerosols for inhalation therapy are generally produced with mean geometric diameters primarily in the range of less than 5 micrometers. Ganderton, D., J Biopharmaceutical Sciences, 3: 101-105 (1992); and Gonda, I. "Physico-Chemical Principles in Aerosol Delivery," in Topics in Pharmaceutical Sciences 1991, Crommelin, D. J. and K. K. Midha, Eds., Medpharm Scientific Publishers, Stuttgart, pp. 95-115, 1992. Large "carrier" particles (containing no drug) have been co-delivered with therapeutic aerosols to aid in achieving efficient aerosolization among other possible benefits. French, D. L., Edwards, D. A. and Niven, R. W., J. Aerosol ScL, 27: 769-783 (1996).

Drugs currently administered by inhalation come primarily as liquid aerosol formulations. However, many drugs and excipients, especially proteins, peptides (Liu, R., et al., Biotechnol. Bioeng., 37: 177-184 (1991)), and biodegradable carriers such as poly(lactide-co-glycolides) (PLGA), are unstable in aqueous environments for extended periods of time. This can make storage as a liquid formulation problematic. In addition, protein denaturation can occur during aerosolization with liquid formulations. Considering these and other limitations, dry powder formulations (DPF's) are gaining increased interest as aerosol formulations for pulmonary delivery. Darnms, B. and W. Bains, Nature Biotechnology (1996); Kobayashi, S., et al, Pharm. Res., 13(1): 80-83 (1996); and Timsina, M., et al., hit. J. Pharm., 101: 1-13 (1994). However, among the disadvantages of DPF's is that powders of ultrafine particulates usually have poor flowability and aerosolization properties, leading to relatively low respirable fractions of aerosol, which are the fractions of inhaled aerosol that escape deposition in the mouth and throat. Gonda, I., in Topics in Pharmaceutical Sciences 1991, D. Crommelin and K. Midha, Editors, Stuttgart: Medpharm Scientific Publishers, 95-117 (1992). A primary concern with many aerosols is particulate aggregation caused by particle-particle interactions, such as hydrophobic, electrostatic, and capillary interactions. The present invention aims to address these issues.

Thus, in a further aspect, the invention provides an inhalation device comprising microparticles of the first aspect, or composition, of the invention. The device may be selected from a dry powder inhalation device and a metered dose inhaler.

In a further aspect of the invention the composition is obtained by preparing an aqueous solution of microparticles, or sulfhydryl (SH) compound, and stabilising agent and evaporating the water from the solution. Preferably the evaporating step is by spray drying.

Thus, a further aspect of the invention provides a process for preparing a composition according to the invention comprising preparing an aqueous solution of microparticles, or sulfhydryl (SH) compound, and stabilising agent and evaporating water from the aqueous solution. Preferably the evaporating step is by spray drying.

The microparticles according to the invention may be in the form of a dry powder. The microparticles may release an effective amount of a sulfhydryl (SH) compound, over a duration of at least two hours from inhalation of said microparticles by a human subject. In a preferred embodiment, substantially all of the Sulphur-containing compound is released by 24 hours from inhalation of said microparticles by a human subject.

Microparticles are convenient to administer, thereby enhancing the extent of patient compliance. The microparticles, or composition, of the invention may be administered in a single puff. Alternatively, the microparticles are formulated to provide sustained release of cysteamine. The microparticles may facilitate local delivery of cysteamine to the lungs or systemic delivery via the lungs.

The microparticles, or compositions, of the invention may also be administered intranasally or by inhalation and may be delivered in the form of a dry powder inhaler or an aerosol spray presentation from a pressurised container, pump, spray, atomiser, nebuliser, with or without the use of a suitable propellant. Preferably the microparticles, or compositions, of the invention are administered to the respiratory tract.

As used herein, the terms "comprise," "comprising," "include," and "including" are intended to be open, non-limiting terms, unless the contrary is expressly indicated.

The invention will now be described by way of example only with reference to the following figures:

FIG. 1 is a graph showing Particle size distribution in batch 57#08a;

Figure 4:
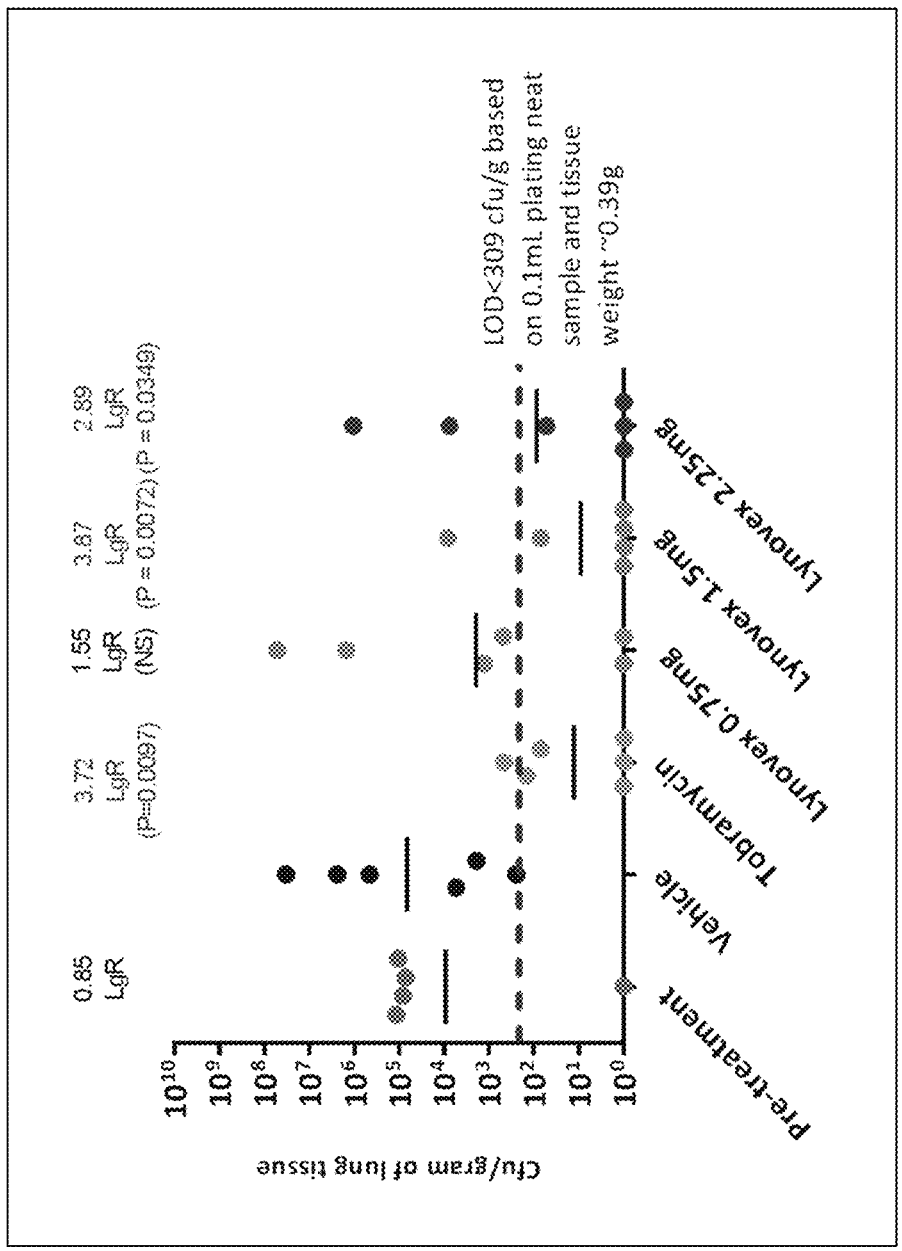
Figure 5:
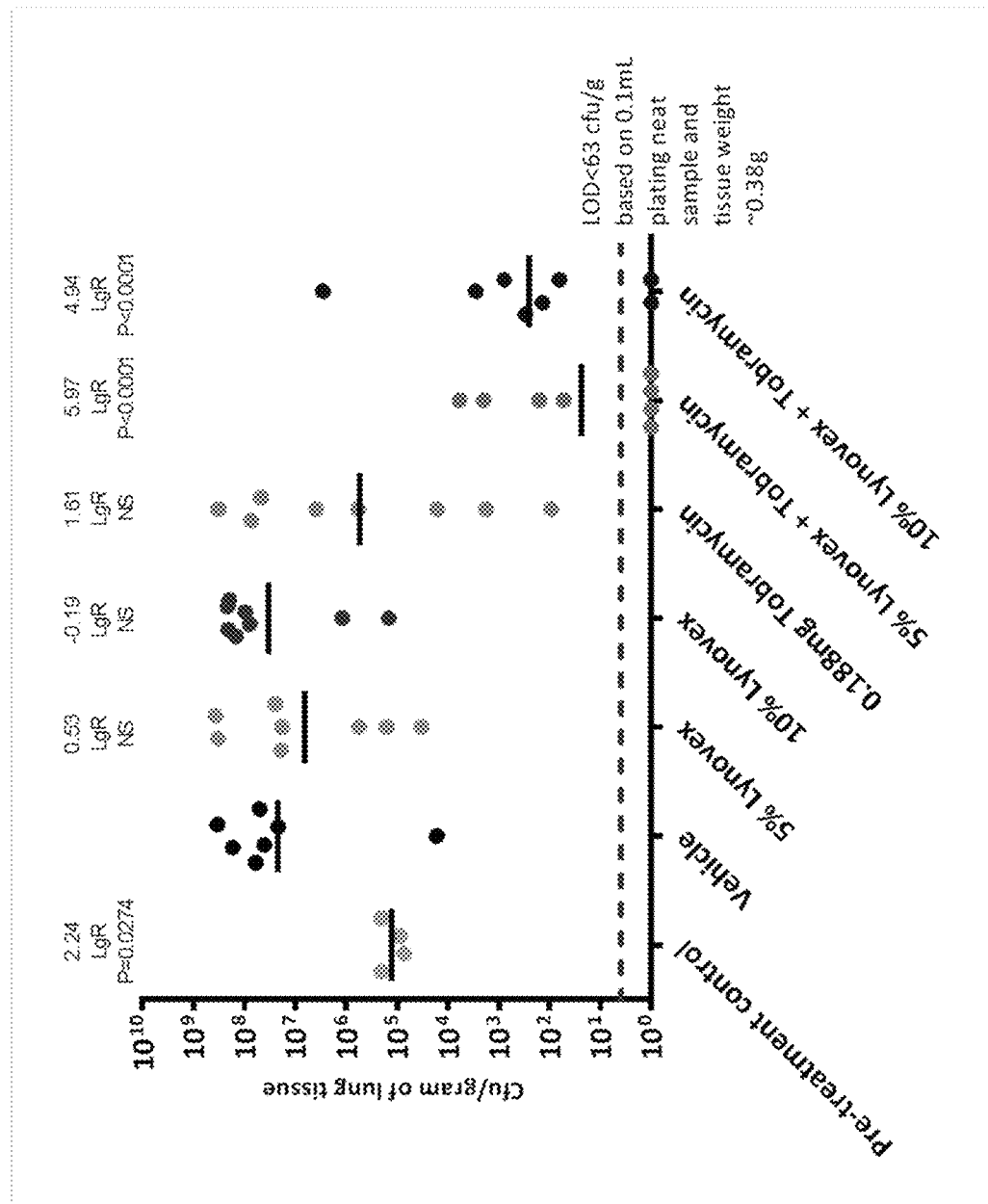
Figure 6:
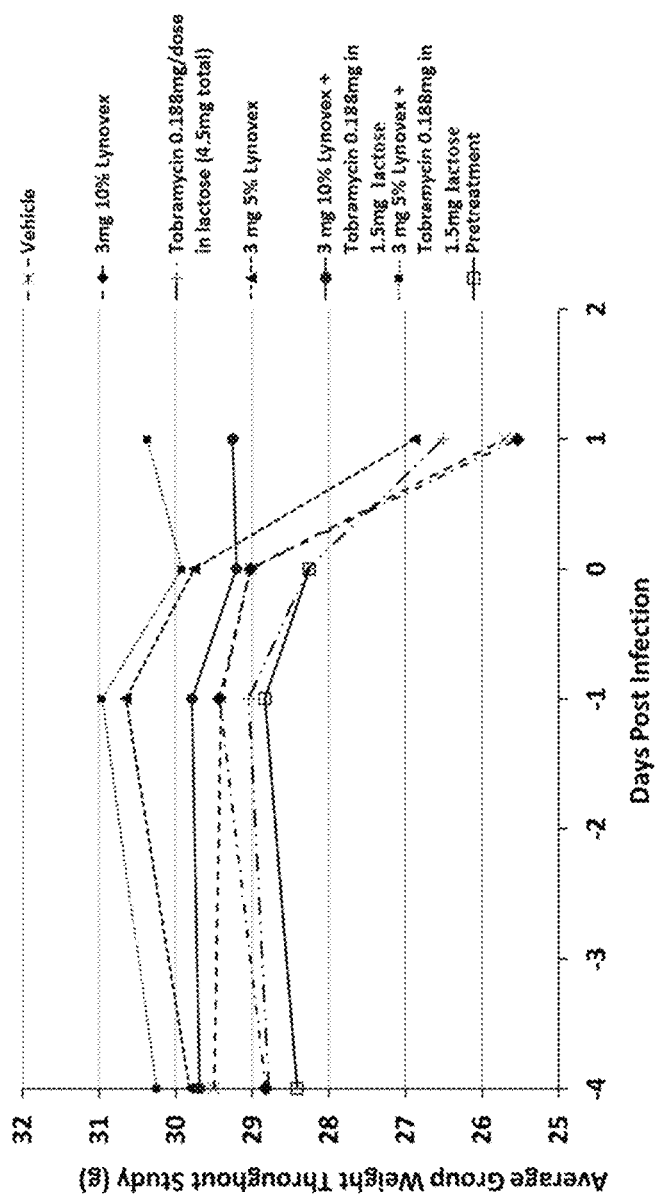

FIG. 4. Lynovex/lactose study demonstrating reduction in *Pseudomonas* lung burden;

FIG. 5. Lynovex (cysteamine) and Tobramycin combination resulting in reduced lung burden;

FIG. 6. Mouse weight does not reduce in the presence of a combination of Lynovex and Tobramycin.

EXAMPLES

Example 1: Spray Drying as a Potential Formulation Technique for the Delivery of Cysteamine Bitartrate by Oral Inhalation Materials Cysteamine Bitartrate: Manufactured by Recordati, batch number 140514-1 was supplied by Nova Biotics.

Oleic Acid: Fluka, 75096-1L, lot number BCBN9185V.

Water: Deionized, Millipore, RiOs 5 system, serial number F8HN7 8491K.

L-Leucine: Sigma, L-8000, lot number 91k0906.

Trehalose: Sigma, T9449-1006, Lot number 011M7000N.

Methods:

Initial spray drying studies using solutions of cysteamine bitartrate formulated with oleic acid and trehalose Several batches of cysteamine bitartrate were produced by spray drying solutions containing the active ingredient alone and with added trehalose and oleic acid (added as a potential taste masking agent).

Cysteaminine bitartrate was allowed to warm to room temperature for 30 minutes before opening. For each batch to be spray dried, 100 mg cysteamine bitartrate powder was added to 10 ml deionised water, to give a total solids concentration of 1% w/v. This was stirred until fully dissolved.

Additional excipients (oleic acid and trehalose) were added to the cysteamine bitartrate solution to assess their impact on the powder properties after spray drying. The solutions were spray dried using a Buchi B290 spray dryer, fitted with a high-efficiency cyclone and a Buchi two-fluid nozzle. Full spray drying conditions are given in Table 1 below:

TABLE 1

Spray Drying Conditions
Results from these initial studies confirmed that the presence of oleic acid in the formulation led to poor powder properties and low recoveries.

| | |
|---|---|
| Aspirator | 100% |
| Liquid Feed Rate | 2 ml/minute |
| Atomisation Pressure | 5.5 bar |
| Inlet temperature | See Table 1 |
| Outlet temperature | See Table 1 |

A summary of the batches spray dried is described below in Table 2.

TABLE 2

Production of Initial Feasibility Batches Containing Oleic Acid
Initial spray drying studies using solutions of cysteamine bitartrate formulated with trehalose (no oleic acid)

| Batch | Component A | Component B | Component C | Solvent | Result | Spray Dryer Temp |
|---|---|---|---|---|---|---|
| 052#053 | Cysteamine Bitartrate 95% | Oleic acid 5% | N/A | EtOH:Water, 2:1 | Waxy, glassy solid deposited on the walls of the cyclone | Inlet: 155° C. Outlet: 83° C. |
| 052#055 | Cysteamine Bitartrate 95% | Oleic acid 5% | N/A | EtOH:Water, 2:1 | Waxy, glassy solid deposited on the walls of the cyclone | Inlet: 78° C. Outlet: 48° C. |

TABLE 2-continued

Production of Initial Feasibility Batches Containing Oleic Acid
Initial spray drying studies using solutions of cysteamine bitartrate formulated with trehalose (no oleic acid)

| Batch | Component A | Component B | Component C | Solvent | Result | Spray Dryer Temp |
|---|---|---|---|---|---|---|
| 052#056 | Cysteamine Bitartrate 70% | Oleic acid 5% | Trehalose 25% | EtOH:Water, 2:1 | Waxy, glassy solid deposited on the walls of the cyclone | Inlet: 75° C. Outlet: 46° C. |
| 052#057 | Cysteamine Bitartrate 32.6% | Oleic acid 1.7% | Trehalose 65.7% | EtOH:Water, 2:1 | Waxy, glassy solid deposited on the walls of the cyclone | Inlet: 63° C. Outlet: 40° C. |
| 052#058 | Cysteamine Bitartrate 95% | Oleic acid 5% | N/A | Ethyl Acetate:Water, 5:1 | Waxy, glassy solid deposited on the walls of the cyclone | Inlet: 50° C. Outlet: 36° C. |
| 052#059 | Cysteamine Bitartrate 95% | Oleic acid 5% | N/A | Water:Ethyl acetate (added to crystals of API are formed) | Waxy, glassy solid deposited on the walls of the cyclone | Inlet: 50° C. Outlet: 38° C. |

Based on the spray drying results obtained in 3.1 (below) it was decided to remove oleic acid from the formulation.

Cysteaminine bitartrate was allowed to warm to room temperature for 30 minutes before opening. For each batch to be spray dried, 100 mg cysteamine bitartrate powder was added to 10 ml deionised water, to give a total solids concentration of 1% w/v. This was stirred until fully dissolved.

Trehalose was added to the cysteamine bitartrate solution to assess its impact on the properties of the spray dried powder. The solutions were spray dried using a Buchi B290 spray dryer, fitted with a high-efficiency cyclone and a Buchi two-fluid nozzle. Full spray drying conditions are given in Table 3 below.

TABLE 3

| Spray Drying Conditions | |
|---|---|
| Aspirator | 100% |
| Liquid Feed Rate | 2 ml/minute |
| Atomisation Pressure | 5.5 bar |
| Inlet temperature | See Table 4 |
| Outlet temperature | See Table 4 |

A summary of the batches spray dried is described below in Table 4 below.

TABLE 4

Spray Drying Conditions for Trehalose Formulations
Spray drying cysteamine bitartrate formulated with Trehalose and L-Leucine
(spray dried batch number 052#155, 052#140, 052#121 with Leucine 052#122 without Leucine)

| Batch | Component A | Component B | Component C | Solvent | Result | Spray Dryer Temp |
|---|---|---|---|---|---|---|
| 052#060* | Cysteamine Bitartrate 10% | Trehalose 90% | N/A | Water | White powder. | Inlet: 81° C. Outlet: 42° C. |
| 052#062 | Cysteamine Bitartrate 50% | Trehalose 50% | N/A | Water | Waxy, glassy solid deposited on the walls of the cyclone | Inlet: 82° C. Outlet: 44° C. |
| 052#063 | Cysteamine Bitartrate 25% | Trehalose 75% | N/A | Water | Dry white powder. | Inlet: 114° C. Outlet: 61° C. |
| 052#064 | Cysteamine Bitartrate 25% | Trehalose 75% | N/A | Water | Dry white powder. | Inlet: 136° C. Outlet: 71° C. |
| 052#65 | Cysteamine Bitartrate 25% | Trehalose 75% | N/A | Water | Dry white powder. | Inlet: 162° C. Outlet: 79° C. |
| 052#66 | Cysteamine Bitartrate 35% | Trehalose 65% | N/A | Water | Wet looking powder. Not free-flowing. | Inlet: 148° C. Outlet: 70° C. |

TABLE 4-continued

Spray Drying Conditions for Trehalose Formulations
Spray drying cysteamine bitartrate formulated with Trehalose and L-Leucine
(spray dried batch number 052#155, 052#140, 052#121 with Leucine 052#122 without Leucine)

| Batch | Component A | Component B | Component C | Solvent | Result | Spray Dryer Temp |
|---|---|---|---|---|---|---|
| 52#67 | Cysteamine Bitartrate 30% | Trehalose 70% | N/A | Water | Damp looking powder. Forms aggregates. | Inlet: 147° C. Outlet: 72° C. |
| 052#097* | Cysteamine Bitartrate 25% | Trehalose 75% | N/A | Water | Dry white powder. | Inlet: 121° C. Outlet: 71° C. Spray pressure 5.5 Bar |

*Used to generate additional data

In order to further improve the properties of the spray dried powder, L-leucine was added to the formulation.

Cysteaminine bitartrate was allowed to warm to room temperature for 30 minutes before opening. 100 mg Cysteamine Bitartrate powder, 50 mg of L-Leucine and 850 mg of Trehalose were added to 10 ml deionised water, to give a total solids concentration of 10% w/v. This was stirred until fully dissolved. Batches 052#140 and 052#155 were scaled to produce a 2 g batch size.

The solution was spray dried using a Buchi B290 spray dryer, fitted with a high-efficiency cyclone and a Buchi two-fluid nozzle. Full spray drying conditions are given in Table 5 below.

TABLE 5

Spray Drying Conditions

| Aspirator | 100% |
|---|---|
| Liquid Feed Rate | 2 ml/minute |
| Atomisation Pressure | 5.5 bar |
| Inlet temperature | 184° C. |
| Outlet temperature | 78° C. |

Following spray drying, the moisture content of the product was reduced further by secondary vacuum drying, at ambient temperature, overnight. The final product was then stored in a sealed glass vial prior to capsule filling. The solutions spray dried are summarised in Table 6 below.

TABLE 6

Spray drying of Cysteamine Bitartrate formulations containing L-leucine
Particle size analysis

| Solution Number | Weight of Cysteaminine Bitartrate | Weight of Trehalose | Weight of L-Leucine | Volume of deionised water | Spray dried powder reference |
|---|---|---|---|---|---|
| 1 | 100 mg | 850 mg | 50 mg | 10 ml | 052#121 |
| 2 | 100 mg | 900 mg | 0 mg | 10 ml | 052#122 |
| 3 | 200 mg | 1700 mg | 100 mg | 20 ml | 052#140 |
| 4 | 200 mg | 1700 mg | 100 mg | 20 ml | 052#155* |

*Collected as two batches of approximately 1 g

Particle size analysis was performed using a SympaTec HELOS particle size analyser with a RODOS disperser. Approximately 50 mg of formulation was fed into the hopper. Dispersal was achieved using compressed air at a pressure of 2 bar. All instrument settings are detailed on the particle size analysis reports in appendix 1 (data not shown).

Aerodynamic Particle Size Analysis by Andersen Cascade Impactor

The aerodynamic particle size of the spray dried powder was determined using a Copley Scientific 8 stage Andersen cascade impactor (ACI) fitted with a 60 l/minute pre-separator and stages-1 to 6. The method was as described in the US Pharmacopiea 29 general chapter <601>, and the European Pharmacopeia 5.1. 2.9.18 (procedure for dry powder inhalers).

The following parameters were used:

Dose: 2× capsules

Capsules: Qualicaps HPMC standard size 3

Device: Plastiape, 3444, COQ, 23970000AA

Plate Coating: None

Airflow: Approximately 60 L/min (determined as a 4 KPa pressure differential across the device).

Actuation Time: Approximately 4 seconds (determined by airflow to equate to a volume of 4 litres)

Plate Washing: 0.1 M sodium phosphate buffer with EDTA, pH 8

Detection: UV at 412 nm using Ellmans reagent to provide a suitable chromophore

Cysteamine bitartrate concentration in the washings was measured at 412 nm as described in section 3.6 below.

The mass of powder deposited at each stage was then calculated using the extinction coefficient determined in section 3.6. By analysing the amount of drug deposited on the various stages, it was then possible, using the dedicated Copley Scientific software, to calculate the Fine Particle Dose (FPD), the Fine Particle Fraction (FPF), the Mass Median Aerodynamic Distribution (MMAD) and Geometric Standard Deviation (GSD) of the peptide particles collected.

The Fine Particle Dose (FPD) was defined as the quantity of drug in the prescribed dose of an inhaled product that is generally considered to be of a size capable of penetrating the lung during inhalation i.e., respirable. This is usually considered to be about 5 microns or less.

The Fine Particle Fraction (FPF) was the FPD expressed as a percentage of the delivered dose.

Quantification of Cysteamine Bitartrate

The quantification of Cysteamine Bitartrate was conducted using a Shimadzu UV-1650PC UV spectrometer. As Cysteamine Bitartrate has no UV chromophore Ellman's Reagent, 5,5-dithiobis(2-nitrobenzoic acid) was used.

Preparation of Reagents

Reaction Buffer: 0.1 M sodium phosphate, pH 8.0, containing 0.1 mM EDTA.

Ellman's Reagent Solution: Dissolve 40 mg Ellman's Reagent in 10 mL
Reaction Buffer
Dissolve 34 mg of Cysteamine Bitartrate in 100 mL of Reaction Buffer to produce a 1.5 mM solution.
Preparation of Standard Curve
Standards were prepared by dissolving Cysteamine Bitartrate in Reaction
Buffer at the following concentrations:

| Standard | Volume of Reaction Buffer mL | Amount of Cysteamine Bitartrate | Final Concentration |
|---|---|---|---|
| A | 100 | 34 mg | 1.5 mM |
| B | 5 | 25 mL of Standard A | 1.25 mM |
| C | 10 | 20 mL of Standard A | 1.0 mM |
| D | 15 | 15 mL of Standard A | 0.75 mM |
| E | 20 | 10 mL of Standard A | 0.5 mM |
| F | 25 | 5 mL of Standard A | 0.25 mM |
| G (Blank) | 30 | 0 mL of Standard A | 0.0 mM |

Table 7 Cysteamine Bitartrate Standards

A set of vials, each containing 50 μL of Ellman's Reagent Solution and 2.5 mL of Reaction Buffer was prepared.

The assay solution or standard (250 μL) was added to the vials prepared in the previous step. The reagents were mixed and analysed on the spectrophotometer immediately. Absorbance was measured at 412 nm.

The values obtained from the standards were used to generate a standard curve. The experimental sample concentration of Cysteamine Bitartrate are determined from this curve.

Results: Initial Studies on the Spray Drying Cysteamine Bitartrate with Oleic Acid and Trehalose Initial studies described in sections 3.1 confirmed that it was not possible to produce a suitable dry powder by spray drying solutions of cysteamine bitartrate containing oleic acid (with and without trehalose). Under all of the conditions used the resultant powder consisted of a glassy, solid material that stuck to the walls of the cyclone and collection jar.

Improved results were obtained when oleic acid was removed from the formulation (see section 3.2). Removal of oleic acid resulted in the production of a fine, white powder (rather than a waxy solid). However the powder was still cohesive and had relatively poor flow properties.

Spray Drying of Cysteamine Bitartrate Formulations Containing Trehalose and L-leucine Powder properties improved when L-leucine was added to the feed solution, resulting in fine white powders. Recoveries (yields) were high; in the range 50-83%. The spray dried powders had acceptable handling properties, and could be easily recovered from the collection vessel with minimal static charge. Formulations containing L-Leucine had a higher % yield and improved flow characteristics over those without.

Yields obtained from spray dried solutions containing L-leucine are summarised in Table 8 below:

TABLE 8

| Spray drying yields from formulations containing L-leucine | | |
|---|---|---|
| Sample Reference | Weight of powder recovered | % Yield** |
| 052#122 | 0.5 g | 50 |
| 052#121 | 0.7 g | 70 |
| 052#140* | 1.6 g | 80 |
| 052#155* | 1.7 g | 83 |

**No residual moisture accounted for
*2 g batch size

Particle Size Analysis of Spray Dried Cysteamine Bitartrate Formulations Containing Trehalose and L-leucine A summary of the particle size data for cysteamine bitartrate formulations containing trehalose and L-leucine are shown in Table 9.

TABLE 9

| Particle size analysis (summary) | | | | |
|---|---|---|---|---|
| Sample | $X_{10}$* (μm) | $X_{50}$** (μm) | $X_{90}$*** (μm) | VMD**** (μm) |
| 052#122 | 0.88 | 2.28 | 4.61 | 2.56 |
| 052#121 | 1.46 | 2.65 | 4.59 | 2.89 |
| 052#140 | 0.93 | 2.75 | 6.39 | 3.34 |
| 052#155A | 0.74 | 1.92 | 4.30 | 2.28 |
| 052#155B | 1.06 | 2.84 | 6.19 | 3.42 |

*10% of microparticles, by volume, below this figure
**50% of microparticles, by volume, below this figure
***90% of microparticles, by volume, below this figure

****Volume mean diameter

Aerodynamic Particle Size Analysis by Anderson Cascade Impactor

A summary of the aerodynamic particle size data for spray dried batches of cysteamine bitartrate, formulated with trehalose and L-leucine is shown in Table 10. Full particle size analysis reports are detailed in appendix 2 (data not shown).

TABLE 10

| Aerodynamic Particle Size | | | | | | | |
|---|---|---|---|---|---|---|---|
| Batch | Capsule A fill wt (mg) | Capsule B fill wt (mg) | Gravimetric quantity of formulation released from device, Capsule A | Gravimetric quantity of formulation released from device, Capsule B | Mass of API recovered from the ACI | FPD (mg) | FPF (%) |
| 052#121 Run 1 | 132.8 | 130.7 | 120.7 | 121.7 | 11.3 | N/A* | N/A* |
| 052#121 Run 2 | 114.8 | 119.6 | 105.0 | 109.5 | 18.5 | 6.9 | 37.7 |

TABLE 10-continued

Aerodynamic Particle Size

| Batch | Capsule A fill wt (mg) | Capsule B fill wt (mg) | Gravimetric quantity of formulation released from device, Capsule A | Gravimetric quantity of formulation released from device, Capsule B | Mass of API recovered from the ACI | FPD (mg) | FPF (%) |
|---|---|---|---|---|---|---|---|
| 052#122 | 84.0 | 75.2 | 54.8 | 54.9 | 11.2 | 3.0 | 27.0 |
| 052#140 Run 1 | 105.9 | 114.1 | 105.0 | 109.5 | 23.1 | 4.5 | 19.6 |
| 052#140 Run 2 | 96.9 | 100.9 | 90.2 | 93.4 | 25.9 | 5.6 | 21.5 |
| 052#155 Run 1 | 82.7 | 84.9 | 76.6 | 41.7 | 14.0 | 6.06 | 43.2 |
| 052#155 Run 2 | 96.2 | 94.3 | 89.5 | 87.8 | 15.3 | 3.6 | 23.7 |

*Not included due to changes within the recovery process analytical method.

CONCLUSIONS

Cysteamine Bitartrate was successfully spray dried with trehalose and with, or without L-leucine. In these studies, a formulation containing cysteamine bitartrate (10% w/w), trehalose (85% w/w) and L-Leucine(5% w/w) were superior in terms of powder recoveries, handling properties and drug loading into the capsules.

The improved powder handling characteristics of the cysteamine bitartrate/trehalose/leucine formulations were translated into an increase in the Fine Particle Fraction (FPF), especially with formulations containing 5% Leucine.

Initial feasibility studies on DPI delivery confirm the spray dried powders can be delivered using commercially available DPI's without a lactose carrier. The initial feasibility studies used spray dried powders provided with a FPF between 20% and 40% and a FPM between 3 and 6.9 mg delivered from two capsules.

Example 2: Production of Spray Dried Cysteamine Bitartrate Formulations for In Vivo Testing Materials Cysteamine bitartrate was supplied by NovaBiotics (Recordati 140514-1). All other reagents were analytical grade, supplied by Sigma.

Methods

Spray Drying of Cysteamine Bitartrate Formulations

Cysteamine bitartrate 5% (w/w), L-leucine 5% (w/w), mannitol 90% (w/w) (Batch 57#08a)

The cysteamine bitartrate powder was warmed to room temperature for 30 minutes before opening. A solution containing 0.1 g cysteamine bitartrate powder, 0.1 g of L-Leucine and 1.8 g of mannitol was prepared in 20 ml deionised water, to give a total solids concentration of 10% w/v. This was stirred until fully dissolved.

The solution was spray dried using a Buchi B290 spray dryer, fitted with a high-efficiency cyclone and a Buchi two-fluid nozzle. Full spray drying conditions are given in Table 11 below

TABLE 11

| Spray drying conditions of Batch 57#08a | |
|---|---|
| Aspirator | 100% |
| Liquid Feed Rate | 2 ml/minute |

TABLE 11-continued

| Spray drying conditions of Batch 57#08a | |
|---|---|
| Atomisation Pressure | 5.5 bar |
| Inlet temperature | 104° C. |
| Outlet temperature | 58° C. |

Following spray drying, the powder was collected and stored in a glass vial using laboratory film and foil over-wrapped within a protective environment with a % RH <10%

Cysteamine Bitartrate 10% (w/w), L-leucine 5% (w/w), mannitol 85% (w/w) (Batch 57#08b)

The cysteamine bitartrate powder was warmed to room temperature for 30 minutes before opening. A solution containing 0.2 g cysteamine bitartrate powder, 0.1 g of L-Leucine and 1.7 g of mannitol was prepared in 20 ml deionised water, to give a total solids concentration of 10% w/v. This was stirred until fully dissolved.

The solution was spray dried using a Buchi B290 spray dryer, fitted with a high-efficiency cyclone and a Buchi two-fluid nozzle. Full spray drying conditions are given in Table 12 below

TABLE 12

| Spray drying conditions of Batch 57#08b | |
|---|---|
| Aspirator | 100% |
| Liquid Feed Rate | 2 ml/minute |
| Atomisation Pressure | 5.5 bar |
| Inlet temperature | 106° C. |
| Outlet temperature | 55° C. |

Following spray drying, the powder was collected and stored in a glass vial using laboratory film and foil over-wrapped within a protective environment with a % RH <10%

Placebo Batch Containing L-leucine 5% (w/w),) mannitol 95% (w/w) (Batch 57#07)

A solution containing 0.1 g of L-Leucine and 1.9 g of mannitol was prepared in 20 ml deionised water, to give a total solids concentration of 10% w/v. This was stirred until fully dissolved.

The solution was spray dried using a Buchi B290 spray dryer, fitted with a high-efficiency cyclone and a Buchi two-fluid nozzle. Full spray drying conditions are given in Table 13 below

TABLE 13

Spray drying conditions of Batch 57# 07

| | |
|---|---|
| Aspirator | 100% |
| Liquid Feed Rate | 2 ml/minute |
| Atomisation Pressure | 5.5 bar |
| Inlet temperature | 100° C. |
| Outlet temperature | 64° C. |

Following spray drying, the powder was collected and stored in a glass vial using laboratory film and foil over-wrapped within a protective environment with a % RH <10%

Particle Size Analysis

Particle size analysis was performed using a SympaTec HELOS particle size analyser with a RODOS disperser. Approximately 50 mg spray dried cysteamine bitartrate formulation was placed on the vibrating feeder and fed into the hopper. Dispersal was achieved using compressed air at a pressure of 2 bar.

Analysis of Cysteamine Bitartrate Content in Spray Dried Powders

The quantification of Cysteamine Bitartrate was conducted using a Shimadzu UV-1650PC UV spectrometer. As Cysteamine Bitartrate has no UV chromophore Ellman's Reagent, 5,5-dithiobis(2-nitrobenzoic acid) was used to measure the sulphydryl group on the cysteamine.

Preparation of Reagents

Reaction Buffer: 0.1 M sodium phosphate, pH 8.0, containing 0.1 mM EDTA.

Ellman's Reagent Solution: Dissolve 40 mg Ellman's Reagent in 10 mL Reaction Buffer Dissolve 34 mg of Cysteamine Bitartrate in 100 mL of Reaction Buffer to produce a 1.5 mM solution.

Preparation of Standard Curve

Standards were prepared by dissolving Cysteamine Bitartrate in Reaction

Buffer at the concentrations shown in Table 14:

TABLE 14

Cysteamine bitartrate standards

| Standard | Volume of Reaction Buffer mL | Amount of Cysteamine Bitartrate | Final Concentration |
|---|---|---|---|
| A | 100 | 34 mg | 1.5 mM |
| B | 5 | 25 mL of Standard A | 1.25 mM |
| C | 10 | 20 mL of Standard A | 1.0 mM |
| D | 15 | 15 mL of Standard A | 0.75 mM |
| E | 20 | 10 mL of Standard A | 0.5 mM |
| F | 25 | 5 mL of Standard A | 0.25 mM |
| G (Blank) | 30 | 0 mL of Standard A | 0.0 mM |

A set of vials, each containing 50 µL of Ellman's Reagent Solution and 2.5 mL of Reaction Buffer was prepared.

The assay solution or standard (250 µL) was added to the vials prepared in the previous step. The reagents were mixed and analysed on the spectrophotometer immediately. Absorbance was measured at 412 nm.

The values obtained from the standards were used to generate a standard curve. The experimental sample concentration of cysteamine bitartrate are determined from this curve.

Analysis of Cysteamine Content in Feed Solutions and Spray Dried Powders

The cysteamine bitartrate content was measured in each of the feed solutions used to produce the two spray dried batches. A 100 µL aliquot of each solution was diluted into 10 ml of DI water to produce a solution that fell within the linear region of the standard curve. The samples were analysed as described in section 3.3.2 and cysteamine bitartrate concentration determined.

The cysteamine bitartrate content was measured in the two spray dried formulations. A 50 mg sample of each powder was diluted into 0.5 ml DI water. A 100 µL aliquot was diluted into 10 ml of DI water to produce a solution that fell within the linear region of the standard curve. The samples were analysed as described in section 3.3.2 and cysteamine bitartrate concentration determined.

Results and Discussion

Spray Drying of Cysteamine Bitartrate Formulations

All feed solution was successfully spray dried, resulting in a fine white powder. Recoveries are summarised in Table 15 below:

TABLE 15

Recovery of spray dried cysteamine formulations

| Batch No | Amount spray dried (g) | Amount recovered (g) | Yield (%) |
|---|---|---|---|
| 57#08a | 2 g | 1.0 | 50 |
| 57#08b | 2 g | 0.75 | 38 |
| 57#07 (placebo) | 2 g | 1.1 | 55 |

Recoveries for batches were lower than anticipated, however this is likely to be due to the small batch size (2 g). All powders had good handling properties, however it was noticed that the 10% cysteamine formulation was slightly more cohesive than the 5% formulation.

Particle Size Analysis

Figure 1:
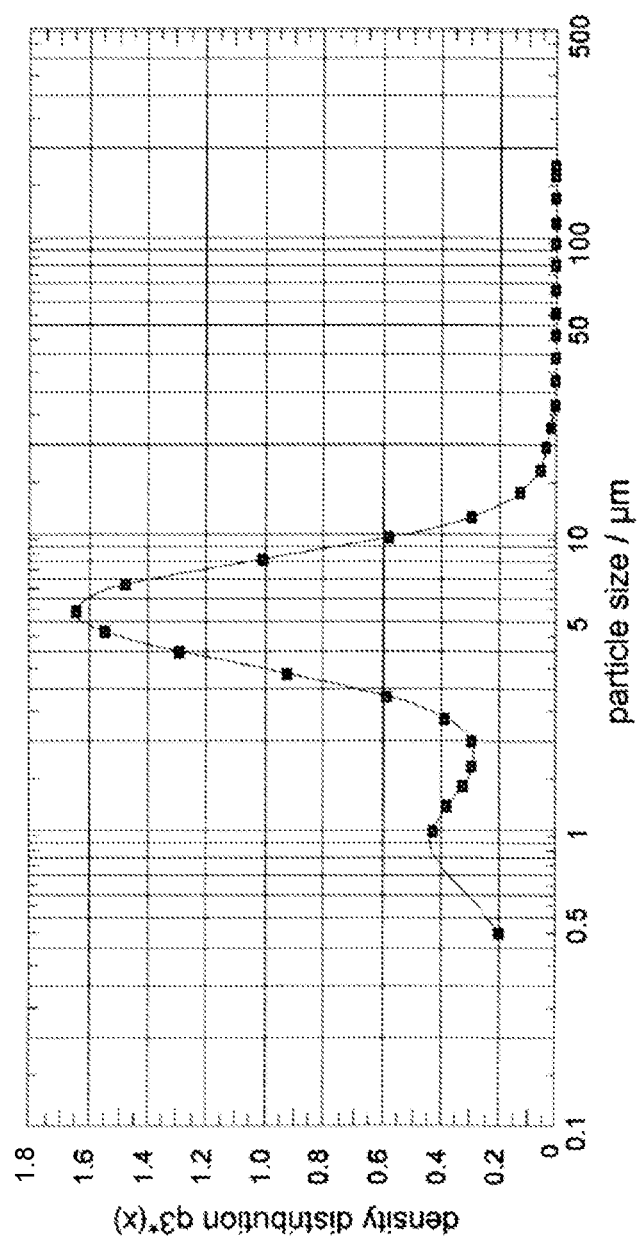
Figure 2:
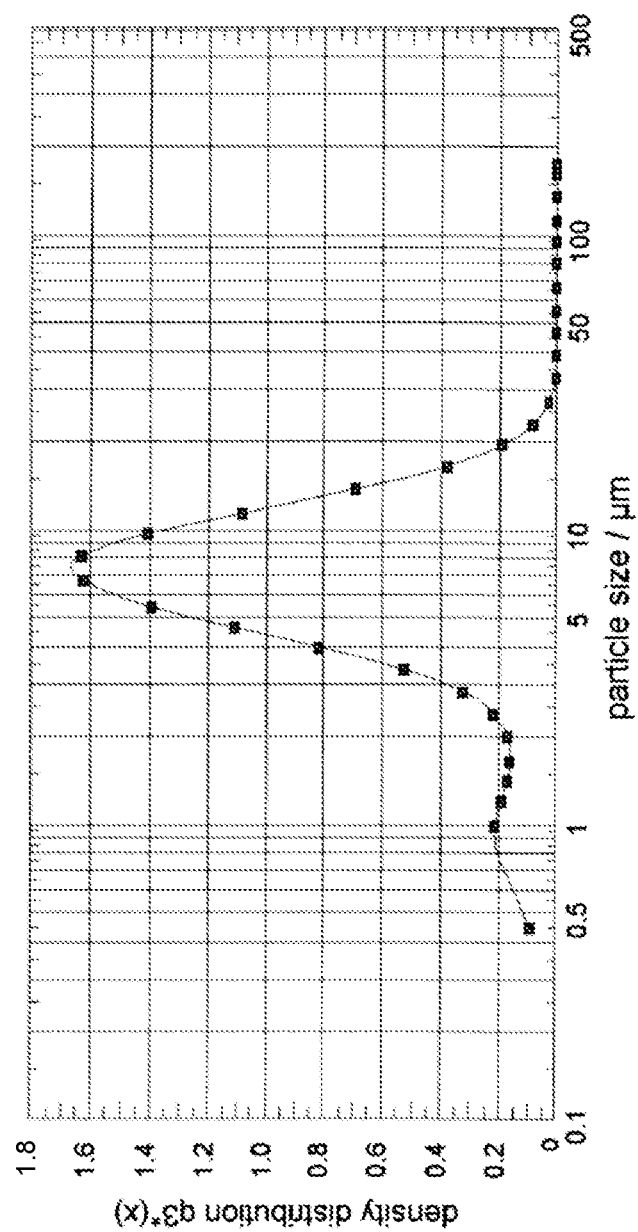
FIG. 2 is a graph showing Particle size distribution in batch 57#08b.
Figure 3:
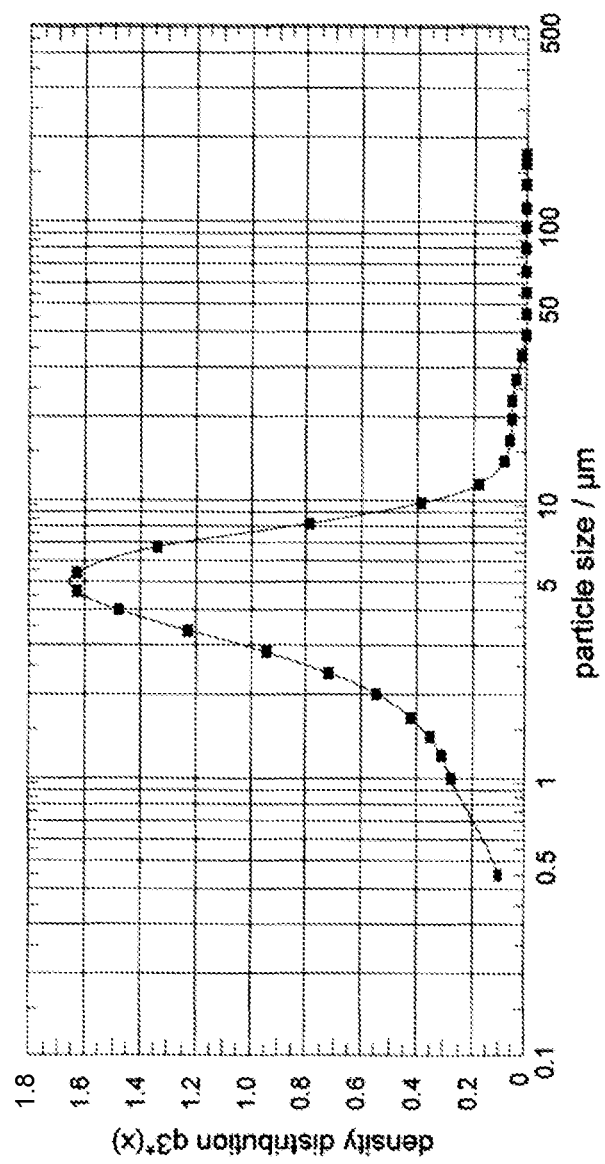
FIG. 3 is a graph showing Particle size distribution in batch 57#07 (placebo)

A summary of the particle size data for all time points is shown in Table 16 and representative particle size distributions are shown in FIGS. 1-3.

TABLE 16

Particle size analysis (summary)

| Batch | $X_{10}$* (µm) | $X_{50}$** (µm) | $X_{90}$*** (µm) | VMD**** (µm) |
|---|---|---|---|---|
| 57#08a | 0.85 | 4.51 | 8.58 | 4.73 |
| | 0.90 | 4.34 | 7.95 | 4.48 |
| | 0.90 | 4.41 | 8.27 | 4.75 |
| 57#08b | 1.62 | 6.61 | 12.69 | 7.16 |
| | 1.83 | 6.89 | 13.28 | 7.49 |
| | 1.91 | 6.99 | 13.21 | 7.52 |
| 57#07(placebo) | 1.29 | 4.2 | 7.99 | 4.66 |
| | 1.37 | 4.27 | 8.09 | 4.73 |
| | 2.68 | 4.49 | 7.38 | 6.72 |

*10% of microparticles, by volume, below this figure
**50% of microparticles, by volume, below this figure
***90% of microparticles, by volume, below this figure
****Volume mean diameter Examples of the size distributions obtained for each batch are shown in FIGS. 1-3.

Determination of Cysteamine Content in Feed Solution and in Spray Dried Powders

Both the spray dryer feed solution and the spray dried powders produced were analysed for cysteamine content. The results obtained are shown in Table 17 below

TABLE 17

Cysteamine content in feed solutions and spray dried powders

| Sample | Target concentration | Measured concentration |
| --- | --- | --- |
| Batch 57#08a (feed solution) | 5% (w/v) | 5.9% (w/v) |
| Batch 57#08a (spray dried powder) | 5% (w/w) | 5.9% (w/w) |
| Batch 57#08b (feed solution) | 10% (w/v) | 11.5% (w/v) |
| Batch 57#08b (spray dried powder) | 10% (w/w) | 11.7% (w/w) |

In all samples the measured concentration was higher than the expected concentration based on the theoretical content.

Example 3: Assessment of Efficacy of Lynovex (Cysteamine) Prep in a Mouse IN Neutropenic Model of *Pseudomonas Aeruginosa* ATCC 27853 (Lung Burden Model)

Chemicals

Animals were immunosuppressed/pre-conditioned with either 200 mg/kg or 150 mg/kg cyclophosphamide. Lynovex, chemical name cysteamine, and vehicle were either prepared either as Lynovex and lactose vehicle, or Lynovex and mannitol-based vehicle (both provided by Upperton (Upperton product)). These were prepared for treatment and vehicle-control alone respectively, and in combination. Tobramycin was prepared as an inhalation formulation in lactose. All treatments were administered using a Penn Century device. Phosphate buffered saline (PBS) and *Pseudomonas* selective agar were required for bacterial tissue burden.

Animals

Male CD1 mice (n =6 for treatment groups, plus five in pre-treatment group, totalling 35 mice) were used in this study. On day −4, the mice were immunosuppressed/pre-conditioned with 200 mg/kg cyclophosphamide intraperitoneally; and with 150 mg/kg cyclophosphamide intraperitoneally on day-1. An infection was established with *P. aeruginosa* ATCC27853, with an inoculum of $5\times10^6$ cfu/ml, administered intranasally in a volume of 40 µl following anaesthetisation with a ketamine/xylazine anaesthetic cocktail for 15 minutes, for the Lynovex prepared in lactose study, and an inoculum of $4\times10^6$ for the Upperton Lynovex product.

Treatment. All treatments were administered intratracheally using a Penn Century device.

Lynovex (cysteamine) was administered at 1.5 mg alone, and in combination with lactose at the following concentrations: Lynovex 0.75 mg+2.25 mg lactose powder, Lynovex 1.5 mg+1.5 mg lactose powder, Lynovex 2.25 mg+0.75 mg, along with a vehicle only control of 3 mg lactose. In addition, Tobramycin at 188 µg/dose was administered, as an inhaled formulation which was mixed with lactose to aid measurement. The treatments were administered approximately 5 minutes after infection.

In a different study, Lynovex was administered at the following doses: 3 mg 5% Lynovex and 3 mg 10% Lynovex. Lynovex in combination with Tobramycin as follows: 3 mg 5% Lynovex+Tobramycin 0.188 mg in 1.5 mg vehicle, 3 mg 10% Lynovex+Tobramycin 0.188 mg in 1.5 mg Vehicle (mannitol-based, provided by Upperton) and a Tobramycin only control (0.188 mg/dose in lactose vehicle). The treatments were administered once approximately 10 minutes after infection.

Bacterial Burden in Tissue

The lung tissue burden of each animal, at the clinical end point of 24 h post-infection, was determined. The lungs were homogenised in 2 ml PBS, serially diluted in PBS and plated onto *Pseudomonas* selective agar before quantification after 24-48 h at 37° C.

With the Lynovex/Lactose study, a variable infection was achieved in the lungs of the mice infected with *P. aeruginosa* ATCC27853. Intratracheal dosing with 0.188 mg of the inhalation formulation of Tobramycin resulted in a statistically significant reduction in lung burden when compared with vehicle-treated mice (P=0.0097 Kruskal Wallis test) and 5/6 animals cleared the infection to below the limit of detection. Intratracheal administration of 1.5 mg and 2.25 mg Lynovex also reduced the lung burden compared to vehicle (P=0.0072 and P=0.0349 respectively) with 5/6 and 4/6 mice respectively clearing the infection to below the detection limit (FIG. 4).

In the Lynovex study with the Upperton product, a robust infection was achieved in the lungs of the mice infected with *P. aeruginosa* ATCC27853. Intratracheal dosing with 0.188 mg of the inhalation formulation of Tobramycin resulted in highly variable burdens with an average 1.61 log 10 cfu/g reduction in lung burden when compared with vehicle-treated mice (Kruskal Wallis test). Intratracheal administration of 3 mg of 5% or 10% Lynovex as monotherapy did not reduce the lung burden compared to vehicle. However, combining 5% or 10% Lynovex with 0.188 mg Tobramycin resulted in a decrease in burden compared to vehicle mice (P<0.0001 and P<0.0001, respectively). This reduction was compared to treatment with Tobramycin alone (P<0.0001 for 5% Lynovex+Tobramycin and P<0.0015 for 10% Lynovex+Tobramycin, Kruskal-Wallis test) (FIG. 5).

Additionally, mouse weights were recorded before and after infection. Mice treated with vehicle, Lynovex monotherapy or Tobramycin monotherapy lost weight following infection. In contrast mice treated with the Lynovex+Tobramycin combinations maintained weight after infection indicating they remained relatively healthy post infection (FIG. 6).

It should be noted that the Tobramycin for dry powder inhalation was suspended in lactose rather than mannitol. Suspension in lactose led to clumping of the powder resulting in some difficulties in delivery as many of the Penn Century devices blocked during dosing. The Lynovex suspensions were much easier to administer and all were delivered without issues due to the delivery device becoming blocked. Whilst the reductions in burden in the combination therapy arms are impressive and significantly superior to Tobramycin monotherapy, the data from some mice treated with Tobramycin monotherapy could be suspect due to the difficulty in delivery of the DPI. Even when animals with uncertain Tobramycin treatment are censored the greatly enhanced efficacy of the combination arms still remains.

What is claimed is:

1. A method of treating lung disease comprising administering to a subject suffering from lung disease a composition comprising microparticles wherein the microparticles comprise a sulphur-containing compound and a stabilizing agent, wherein the sulphur-containing compound is selected from the group consisting of cysteamine or cystamine; or a pharmaceutically acceptable salt, hydrate or ester thereof, and combinations thereof, wherein the stabilizing agent is selected from the group consisting of trehalose and sugar alcohols, and wherein the microparticles have a particle size of about 1 micron to about 8 microns.

2. The method of claim 1, wherein the composition further comprises at least one additional pharmaceutical agent.

3. The method of claim 2, wherein the at least one additional pharmaceutical agent is an antibacterial agent.

4. The method of claim 2, wherein the at least one additional pharmaceutical agent is selected from the group consisting of antibiotics, mucolytic agents, vasodilators, antihypertensive agents, cardiovascular drugs and calcium channel blockers.

5. The method of claim 1, wherein the lung disease is a respiratory disease.

6. The method of claim 5, wherein the respiratory disease is selected from cystic fibrosis, chronic obstructive pulmonary disease, chronic bronchitis, bronchiectasis, emphysema, chronic obstructive airways disease, chronic cough, common cold, influenza, hantavirus, pneumonia, or pleurisy.

7. The method of claim 1, wherein the microparticles have a particle size of about 2 microns to about 8 microns.

8. The method of claim 1, wherein the composition is administered by inhalation or intranasally.

9. The method of claim 1, wherein the microparticles comprise up to 30% w/w of the sulphur-containing compound.

10. The method of claim 1, wherein the microparticles comprise up to 25% w/w of the sulphur-containing compound.

11. The method of claim 1, wherein the microparticles comprise between about 5% w/w and 10% w/w of the sulphur-containing compound.

12. The method of claim 1, wherein the microparticles comprise up to 85% w/w of the stabilizing agent.

13. The method of claim 1, wherein the composition additionally comprises leucine.

14. The method of claim 13, wherein the composition comprises between 1% w/w and 10% w/w of leucine.

15. The method of claim 1, wherein the sugar alcohol is mannitol.

16. The method of claim 1, wherein the composition is in the form of a dry powder.

* * * * *